(12) United States Patent
Breznitz

(10) Patent No.: US 6,632,174 B1
(45) Date of Patent: Oct. 14, 2003

(54) METHOD AND APPARATUS FOR TESTING AND TRAINING COGNITIVE ABILITY

(75) Inventor: Shlomo Breznitz, Haifa (IL)

(73) Assignee: Cognifit LTD (Naiot), Nazrat Ilit (IL)

( * ) Notice: Subject to any disclaimer, the term of this patent is extended or adjusted under 35 U.S.C. 154(b) by 0 days.

(21) Appl. No.: 09/611,974

(22) Filed: Jul. 6, 2000

(51) Int. Cl.[7] .......................... A61B 5/00; G09B 19/00
(52) U.S. Cl. ........................... 600/300; 434/236
(58) Field of Search ................. 600/300–301, 600/558, 544–545, 587; 128/704, 920, 897, 898; 705/2, 3; 434/258, 219, 236–238, 247, 29, 61–62, 64–66, 69, 71, 307 R; 706/11, 45–46

(56) References Cited

U.S. PATENT DOCUMENTS

| | | | |
|---|---|---|---|
| 5,344,324 A | * | 9/1994 | O'Donnell et al. ......... 600/558 |
| 5,687,291 A | | 11/1997 | Smyth |
| 5,772,611 A | | 6/1998 | Hocherman |
| 5,911,581 A | | 6/1999 | Reynolds et al. |
| 6,113,538 A | * | 9/2000 | Bowles et al. ............ 600/300 |
| 6,227,862 B1 | * | 5/2001 | Harkness .................... 434/65 |
| 6,260,022 B1 | * | 7/2001 | Brown ........................ 705/2 |
| 6,280,198 B1 | * | 8/2001 | Calhoun et al. ........... 434/236 |

* cited by examiner

*Primary Examiner*—Max F. Hindenburg
*Assistant Examiner*—Michael Astorino
(74) *Attorney, Agent, or Firm*—Eitan, Pearl, Latzer & Cohen Zedek, LLP

(57) ABSTRACT

A method for testing and/or training cognitive ability, including the steps of testing a preliminary cognitive level of a user and receiving results representative therefrom. According to the results, the cognitive level may then be broken up into separate discrete cognitive skills, and one or more tasks may be created, each task related to each of the separate discrete cognitive skills. The one or more tasks may then be presented to the user and so that a current cognitive level of the user is re-tested, and results representative therefrom are received. This process may be repeated at least one time.

36 Claims, 7 Drawing Sheets

METHOD AND APPARATUS FOR TESTING AND TRAINING COGNITIVE ABILITY

FIELD OF THE INVENTION

The present invention relates generally to methods and apparatus to test, sustain and improve cognitive ability and, in particular, to such methods and apparatus using analysis and training.

BACKGROUND OF THE INVENTION

Our actions are mediated and influenced by our cognitive and psychomotor abilities. From the sophisticated to the mundane, everything we do depends on our capacity to understand and effectively interact with our environment. Consequently, any decline in these capacities has an impact on our quality of life. Cognitive and psychomotor performance declines with head trauma, as well as with advancing age.

Systems have been developed to test cognitive abilities. However, these systems only measure and analyze mental ability, and they fall short of attempting to arrest the effects of aging on cognitive abilities. Thus, there is still a continuing need for endeavors to maintain or improve cognitive abilities.

SUMMARY OF THE PRESENT INVENTION

There is therefore provided, in accordance with a preferred embodiment of the present invention, a method for testing and/or training of cognitive abilities.

There is also provided in accordance with an embodiment of the present invention a method for diagnosing cognitive ability of a user. The method may include presenting a stimulus, receiving a motion Input (generally in response to the stimulus), and analyzing cognitive aspects of the motion input.

The step of presenting may be selected from a group consisting of: presenting a moving stimulus, presenting a stimulus which changes color, presenting a stimulus which changes shape, presenting one or more stimuli and presenting stimuli targeting different senses.

The motion input may be selected from a group consisting of: moving the stimulus, positioning the stimulus, moving a peripheral device to intercept the stimulus, operating a control with discrete states, and adjusting the stimulus.

The stimulus may be selected from a group consisting of: one or more abstract stimuli, one or more meaningful stimuli and a combination of the one or more abstract stimuli with the one or more meaningful stimuli.

The cognitive aspects may be selected from a group consisting of: psychomotor skills perceptual skills, attention skills, memory skills, linguistic skills, decision making/problem solving skills, psychomotor skills, and meta-cogntive skills.

The method may further include determining from the cognitive aspects a cognitive level of the user.

One way to execute the step of analyzing may include testing a preliminary cognitive level of the user and receiving results representative therefrom. The results are then broken up into separate discrete cognitive skills. Then, according to the results, one or more tasks may be created. The one or more tasks may relate to each of the separate discrete cognitive skills and may be presented to the user in order to retest the user for a current cognitive level. Generally, results are received representative therefrom.

One way to execute the step of creating may include creating a first task that tests/trains a first cognitive skill, and using the results of the first task as parameters for one or more other tasks.

The method may further include updating the step of presenting in accordance with results from the step of analyzing, and repeating the previous steps one or more times. Additionally included may be the step of differentiating between false positive and false negative errors.

The present invention may be provided on a computer software storage device that includes a program that executes the described method. The method may be used for training and performed repeatedly, such as several times a week. It may also be used to diagnose or treat dementia, Alzheimer's disease, Parkinson disease, Hyperactive and Attention Deficit Disorders, as well as learning disabilities, or used in cognitive rehabilitation following stroke, head injury, and alcohol and drug abuse.

The present method may also include customizing the step of presenting for each user in accordance with results to the step of analyzing and/or to generally optimally challenge the cognitive level of the user. The step of updating may include controlling a selection of the stimulus in order to attempt to avoid frustration of the users.

In accordance with the present invention, there is also provided a method for training cognitive ability. The method includes testing a preliminary cognitive level of a user and receiving results representative therefrom. According to the results, the cognitive level may then be broken up into separate discrete cognitive skills, and one or more tasks may be created, each task related to each of the separate discrete cognitive skills. The one or more tasks may then be presented to the user and so that a current cognitive level of the user is re-tested, and results representative therefrom are received. This process may be repeated at least one time.

The separate discrete cognitive skills may include perceptual skills, attention skills, memory skills, linguistic skills, decision making/problem solving skills, psychomotor skills, and meta-cognitive skills.

Creating the tasks may include creating a first task that trains a first cognitive skill and using results of the first task to control one or more other tasks. The method may also include determining an optimal challenge level based on results from the retesting of the user.

The present Invention may also be used to enhance or postpone decline of short term memory, perceptual abilities, and other cognitive and psychomotor abilities in people of all ages.

There is furthermore provided an embodiment for a system for training cognitive ability. The system may include a motion input device, an output device that provides a stimulus, which may be affected by a user manipulating the Input device, and an analyzer which may analyzes data from the input device and determines therefrom cognitive levels.

The system may further include a voice recording device such as a microphone.

The system may further include a processor that determines from the analyzed data the stimuli appropriate for the cognitive level. The motion input device may be either a mouse, a joystick, a foot pedal, a digital pen, a stylus, a motion pad or a steering wheel.

The analyzed data may be data regarding motor skills, complex/continuous motor skills, time required to move the stimulus, movement smoothness, complex eye hand coordination, hand-hand coordination, and/or eye-foot coordination. The system may include a database for storing the analyzed data, where the data may relate to cognitive norns.

There is yet additionally provided a method for diagnosing cognitive ability of a user, including the steps of testing a cognitive level of a user and comparing the tested cognitive level to the data stored in the database, so as to diagnose diseases/difficulties such as dementia, Alzheimer's disease, Parkinson disease and learning disabilities.

Yet further provided is a method for training driving skills of a user. The method includes the steps of presenting stimuli relevant to driving situations, receiving motion input, from the user in response to the stimulus, analyzing cognitive aspects of the input, interpolating the analyzed aspects into cognitive skills applicable for driving skills, adjusting the stimulus according to the analyzed aspect, and repeating the steps of presenting, receiving, analyzing, interpolating and adjusting one or more times.

The method may further include recording the number and type of mistaken responses and recording the speed of reaction and distinguishing between false positive errors and false negative errors.

BRIEF DESCRIPTION OF THE DRAWINGS

The present invention will be understood and appreciated more fully from the following detailed description taken in conjunction with the drawings in which.

DETAILED DESCRIPTION OF PREFERRED EMBODIMENTS

Figure 1A:
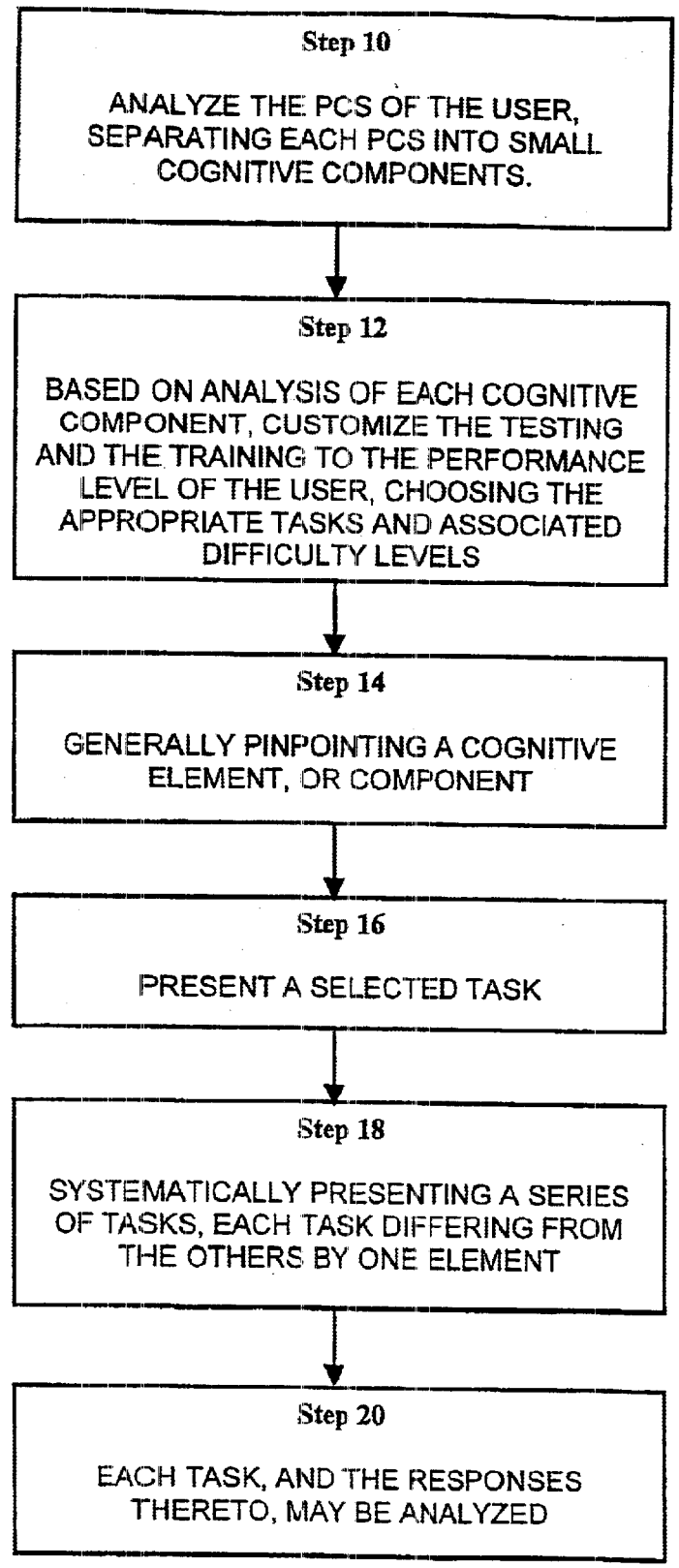
FIGS. 1A and 1B are flow charts of one possible embodiments of the present invention.

In the following detailed description, numerous specific details are set forth in order to provide a thorough understand of the invention. However, it will be understood by those skilled in the art that the present Invention may be practiced without these specific details. In other instances, well-known methods, procedures, elements, and facilities have not been described in detail so as not to obscure the present invention.

The present invention utilizes analysis, mental exercise and intervention in an attempt to increase cognitive abilities, improve speed of reaction, and train both functional cognitive, attentional, perceptual, and linguistic abilities and various aspects of memory. Presented herein are an apparatus and method for measuring and training those abilities using a computer-based module, Normal aging may lead to decline in cognitive skills. One of the described embodiments of the present invention focuses on reducing, postponing, or preventing such age-related decline through computer guided training exercises.

While the present invention may be used with therapy for the aging brain, it applies to all ages and may be used as a training system for youths, mentally challenged individuals, as well as persons in need of cognitive rehabilitation following injury. Thus, other described embodiments focus on the skills associated with developing skills in children and teenagers, or maintaining the cognitive skills needed for driving a vehicle. Yet other embodiments focus on the treatment of mental difficulties, alcohol and drug related decline, or age related dementia.

The invention comprises a system which may be used for the effective measurement and training of psychomotor and cognitive skills. The following is a partial list of skills that may be tested and trained using the present invention: hand-eye coordination, smooth movement, spatial orientation, route planning, mental rotation, speed/distance/time estimation, visual search, attention allocation/focusing, distractibility, split attention, scene perception, simple and choice reaction time, decision-making, risk-taking, short-term memory (STM), location memory, memory for names, information encoding strategies, retrieval from long-term memory (LTM), response to time pressure (TP), ability to inhibit planned action, problem-solving, and linguistic skills.

The embodiments of the invention may be used to train perceptual skills, attention skills, memory skills, linguistic skills, decision-making and problem-solving skills, psychomotor skills and meta-cognitive skills, although it should be understood that the scope of the present invention is in no way limited to these applications.

The present system is based on cognitive science and gerontology, and utilizes advanced computer and electronic technologies in an endeavor to provide measurement of psychomotor and cognitive skills (PCS) in detail that has been impossible until now. It is noted that the provision for motion analysis may provide basis for wider PCS analysis than was possible with binary (yes—no) prior art testing systems.

Figure 1B:
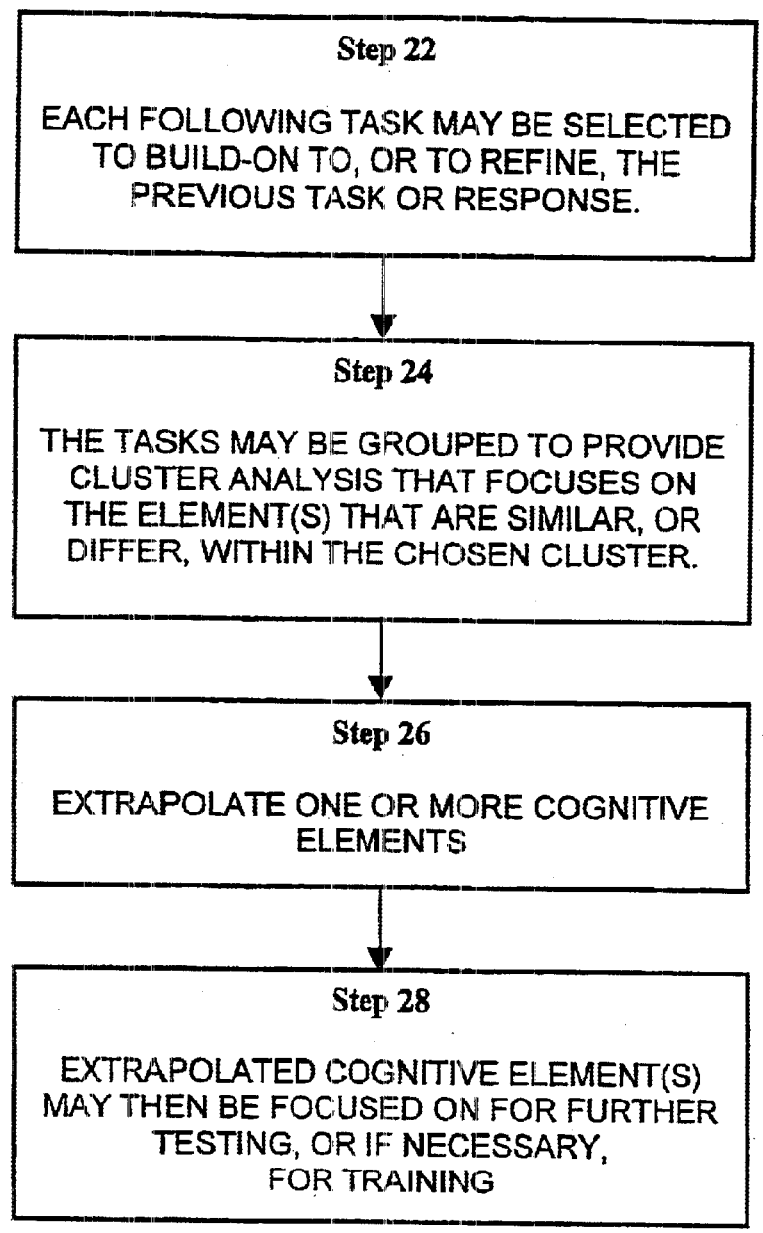

In an embodiment of the present invention, as presented in FIGS. 1A and 1B, initially the present inventive system may analyze the PCS of the user, separating each PCS into small cognitive components (step 10). Then, based on analysis of each cognitive component, the system may customize the testing and the training to the performance level of the user, choosing the appropriate tasks and associated difficulty levels (step 12).

One means to customize the testing and/or training may comprise generally pinpointing a cognitive element, or component (step 14). To do so, a first selected task may be presented (step 16), then systematically, a series of tasks are presented, each task differing from the others by one element (step 18). In one embodiment, each task, and responses thereto, may be analyzed (step 20), and each following task may be selected to build-on-to, or to refine, the previous task or response (step 22). Thus, each task may be used not only for analysis of the individual task, but also as a parameter for defining subsequent tasks.

Typically, the tasks may be grouped to provide cluster analysis that focuses on the elements which are similar, or differ, within the chosen cluster (step 24). In such a manner it possible to extrapolate one or more cognitive elements (step 26). The extrapolated cognitive element(s) may then be focused on for further testing, or if necessary, for training (step 28). Recent scientific evidence indicates that psychomotor and cognitive functioning are significantly enhanced by training.

It should be apparent to those skilled in the art that the present invention may be executed in "real time" allowing for dynamic decisions and analysis, allowing for on-line selection of tasks and training. It should additionally be apparent that the methods described herein for cluster analysis may be performed with one or more tasks, rather than a series of tasks, and may entail analysis of a single cognitive element, or a multiplicity thereof.

It should be noted that since one of the uses of the present invention is to test and/or train persons who may evident deficits or declines in their cognitive ability, it is important to take into account the mental well-being of that user, and define the tasks so as to avoid frustration. As may be observed by those skilled in the arts, it is preferable that aged persons or persons with various cognitive challenges, will be tested and trained at an optimal level, rather than at a level that may either exceed their ability, or produce boredom.

One method of doing so may be to monitor response time and correctness. An indication of sub-optimal challenge that may lead to frustration may be a change of pace and/or an increased number of errors. The change of pace may be either a sudden increase or decrease in speed of response; either one when compounded with an increased number of errors, may indicate frustration. Tasks that are too easy for a user may induce boredom, and will be avoided as well.

Detailed herein below are two possible phases of the present invention: a testing/analysis phase and a training phase. It is noted that sub-phases of the present phases, or other forms thereof, are possible and included within the scope of the invention.

Testing/Analysis

Figure 2:
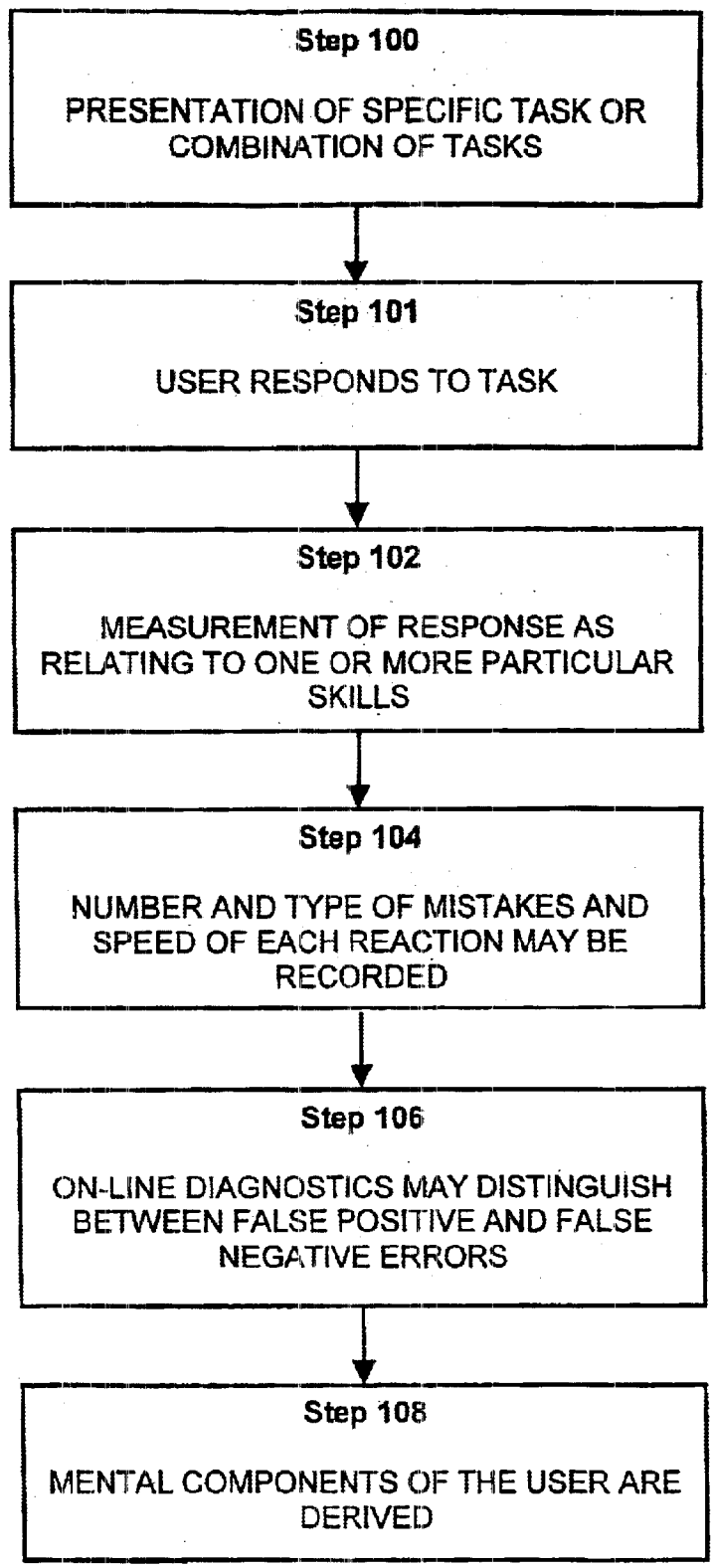
FIGS. 2–4 are flow charts of possible embodiments of testing/diagnosis as per the present invention.

Turning to FIG. 2, a flow chart delineating a method in accordance with the present invention is described. Testing embodiments may be based on computer-controlled presentation of specific tasks or combinations of tasks which presentation may contain stimuli (step 100). As a user responds to the presented task, the system may receive the response(s), including both movements required to perform the task and the final decision thereto, if applicable (step 101). The responses may then be measured as relating to one or more particular skill (step 102). The number and type of errors, the detailed parameters of the movement, as well as the speed of each reaction may be scored (step 104). Diagnostics, which may be on-line, may optionally distinguish (step 106) between two kinds of errors: false positive (decision to take an action where there is no need to) and false negative (decision to not take an action where there is need to), The mental components of the users may be derived (step 108) based on systematic comparisons between the designated task and other tasks belonging to the same diagnostic cluster, where a diagnostic cluster comprises several tasks which share some mental elements, while differing in other elements.

For instance, simple reaction time and decision time, both with and without distraction, may form a diagnostic cluster of 4 tasks (step 100). Thus, for the example detailed in FIG. 2, the effect of distraction on decision time may be calculated by subtracting simple reaction time from decision time for tasks with, as well as without, distractors, and comparing the net result in the two distraction conditions. It is noted that each of the tasks may be used both for its own goal and as a tool for control for other tasks.

An example of such is as follows and as presented in FIG. 3: In testing speed estimation, a user may be presented with a circle crossing the screen from left to right at a particular speed (step 200). Once the circle crosses the screen, a second circle may appear, moving at a different speed than the first one (step 202). The user may be asked to judge which of the balls was moving faster (step 204), and the response is verified for correctness (step 206). The user may also be asked whether or not he is confident in his judgment. If the response was correct, the program may then presents a more difficult task (step 208), i.e. one in which the difference in speed is harder to detect, whereas an incorrect response may lead to the presentation of an easier comparison (step 210). This procedure may be followed until the point is reached at which the users response is correct only 50% of the time, i.e., no better than chance (step 212). This point defines the users "difference threshold", i.e. the percentage difference between the two speeds the user cannot recognize. Determination of the threshold may subsequently be used to control for effects of a variety of factors on speed estimation. Confidence in judgments maybe related to correctness, giving further indication of the level of the particular skill being measured, as well as the user's awareness of his/her skill level.

An additional example is described below and presented in FIG. 4, to which reference is now made. A circle of a target color is presented on a screen, which may be a component of a computer having a mouse or other pointing device connected thereto (step 300). The mouse cursor may be moved by the user towards the target (step 302), which may change into a non-target color as the mouse gets closer (step 304). In step 306, the user may be requested to inhibit the movement. It should be noted that the scope of the invention is in no way limited to this example, and alternative variations of this task are possible and included within the scope of the invention.

Figure 4:
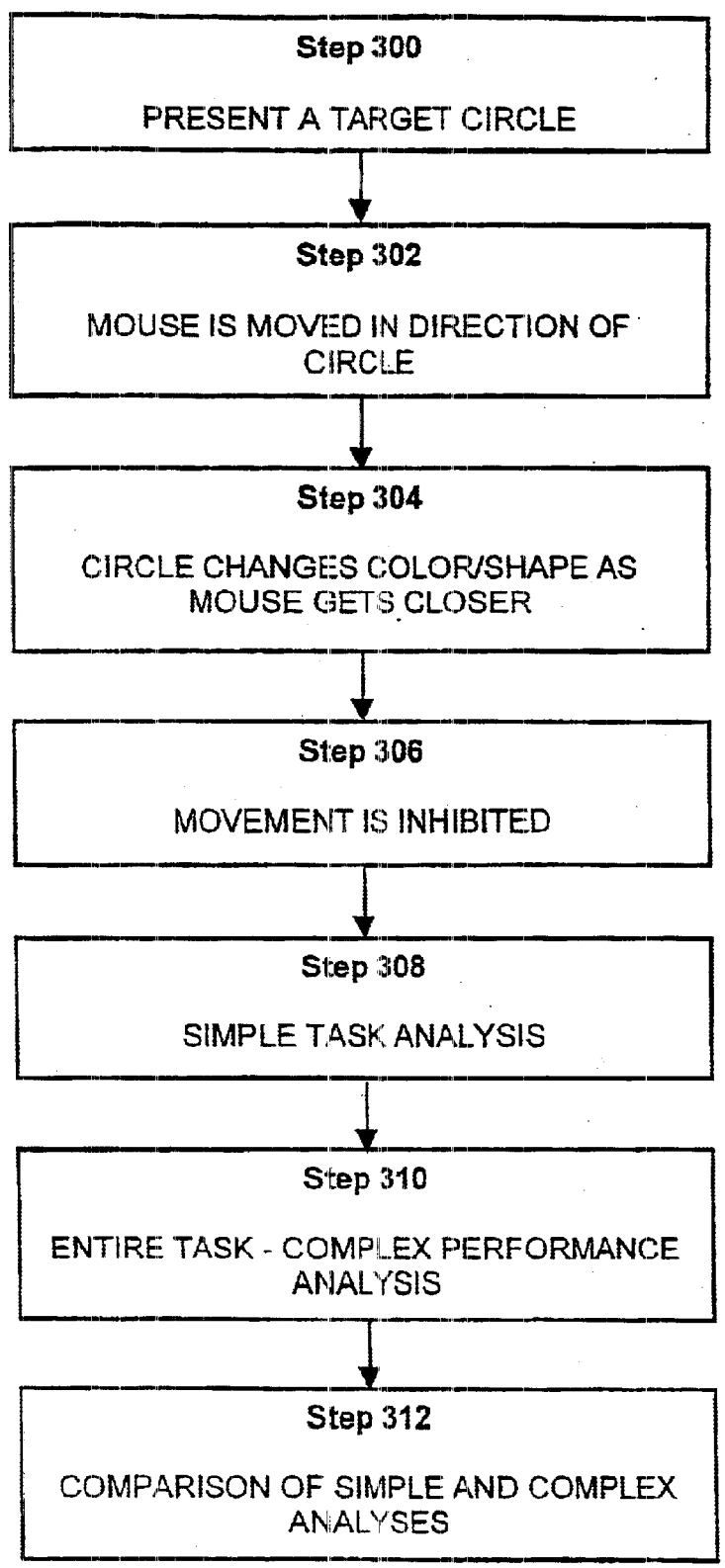

As an example of above mentioned cluster analysis, the task presented in FIG. 4 may then be analyzed both to determine, for example, the inhibition component and to separate this component from motor and perceptual components (step 306). One method of doing so may be to isolate from the entire task (steps 300–306) the single, simple element of clicking on a yellow circle whose color is constant and to perform a cognitive analysis of such (step 308). Next, the complex performance of the entire task may be analyzed, including the hesitation of the user's response along with the direction and speed of the mouse's approach (step 310). The two analyses, complex and simple, may then be compared (step 312) and or used to control for similar mental elements embedded in other tasks.

It is noted that whereas some of the general methods for measurement and analysis of the skills and components as noted above or listed below are methods commonly practiced by those skilled in the art, the specific methods, as well as their combination which allows the isolation of active mental components, is one of the unique elements of the present invention. In one embodiment, the testing and analysis stage may be used to determine the presence of dementia, head injury, stroke effects, and other diagnostic categories, This may be done by cross-validating the test results against currently acceptable diagnostic criteria.

Training

Figure 5:
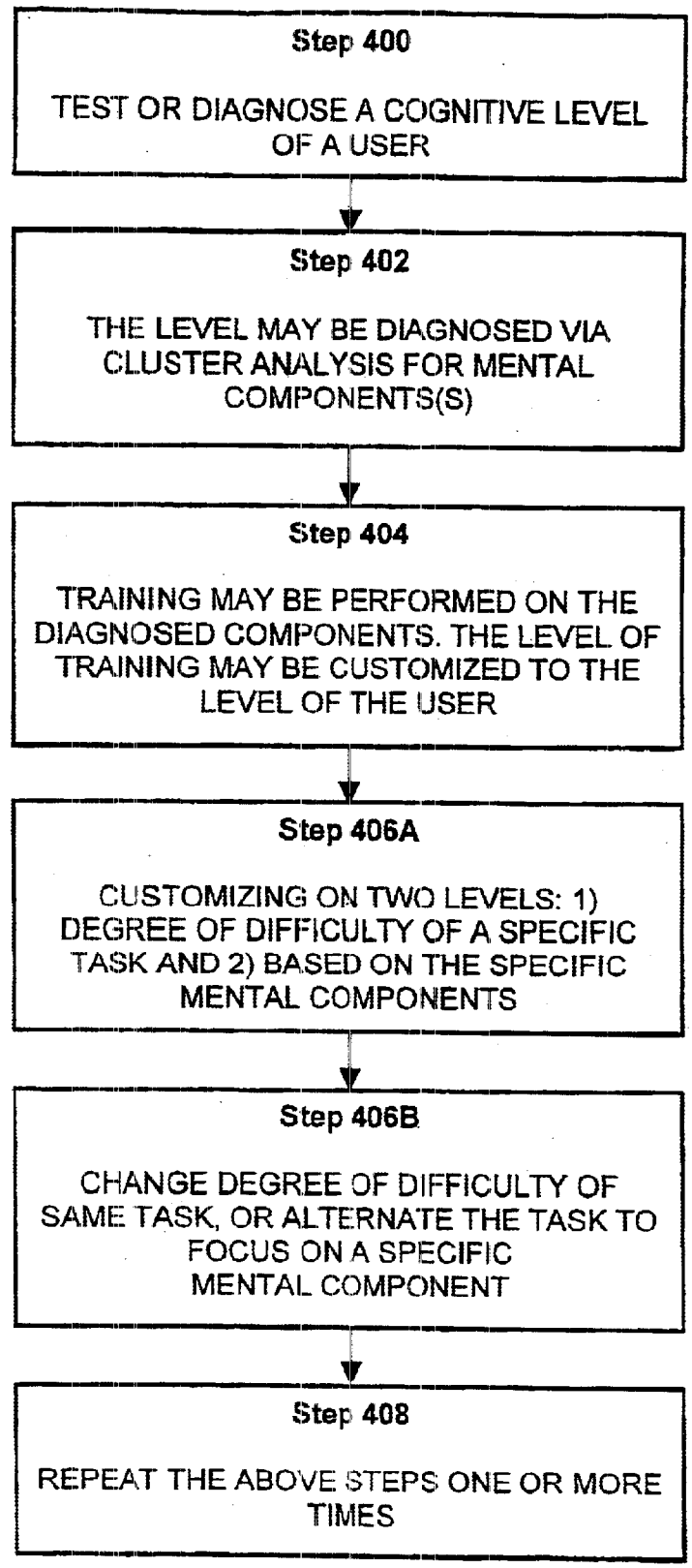
FIGS. 5–6 are flow charts of possible embodiments of training as per the present invention.

The present invention endeavors to adjust the training to the measured performance level of the user. Reference is now made to FIG. 5, a flow chart depicting a possible portion of one training method according to the present invention.

As noted above, it is possible to test or diagnose a cognitive level of a user (step 400). The level may be diagnosed via cluster analysis for mental component(s) (step 402). Training may be performed on these components. The level of training may be customized to the level of the user (step 404).

Customizing, or adjustment, may be performed in two ways; 1) degree of difficulty of a specific task, and/or 2) based on specific mental components, as determined from the diagnosis done earlier (step 406A). As such, adjustment may be accomplished by changing the degree of difficulty of a specific task, such as by altering the pace of the task, or some other element of difficulty. Alternatively, adjustment may entail maintaining the same degree of difficulty, however, alternating the task to train a specific mental component (step 406B). The training may encompass systematic testing of various capabilities at the start, and at various stages of training, and thus, may provide scientific information and a demonstration of its utility for the user. The training may be repeated one or more times (step 408).

The training tasks may involve gaming elements to further enhance the motivation of the user. The tasks preferably may start with easy problems to insure initial success and positive reinforcement, and gradually may increase in the level of challenge. The use of immediate feedback, as well as elements of competition when appropriate, may be included.

The present invention may be customized to the optimal challenge level for the user, based on past and current performance analysis with online dynamic diagnosis of errors and biases, Although various examples are listed herein below, it is noted that there are a variety of ways to train the same basic skills and produce the relevant scientific information. It is additionally preferable to exercise and train several PCSs at the same time.

The present invention may also be used for cognitive rehabilitation following a stroke, a head injury, or other type of trauma-related cognitive decline, as well as alcohol or drug related decline. It is noted that repetitive training may produce improvements and/or stabilization of the cognitive level, wherein training may be performed as often as desired or prescribed, such as 3 times a week.

Some of the skills that may be tested and possible methods for training such are listed herein below. It is noted that the examples given are just a sampling of the possible embodiments of the present invention. As such, the presented stimuli are interchangeable with other stimuli that may be used for similar purposes, and still are included within the principles of this invention. As an example, symbols may be interchanged with road signs, sounds may be interchanged with visual stimuli, circles may be interchanged with other shapes, etc. Stimuli may be either abstract or meaningful stimuli, as appropriate for the task or training presented. As an example, abstract stimuli may be a circle or square, whose purpose may be for the user to observe thereto, and the shape may not be significant. In contrast, meaningful stimuli may be either a known face or a word, whose purpose may be for the user to memorize or identify. In such a case the content stimuli may be meaningful. It should be apparent to those skilled in the art that skills or tasks presented herein with the purpose of testing or training a specific cognitive ability are interchangeable with alternative skills or tasks which perform similar testing and training for similar cognitive abilities.

Additionally, only a sampling of the embodiments below are depicted in the figures presented herein. It will be understood by those skilled in the art, without accompanying figures, the flow of the other presented embodiments as detailed hereinbelow:

Perceptual Skills

One embodiment of the present invention may be used to measure, train and maintain a wide range of perceptual skills, such as: depth perception, contextual perception, peripheral awareness, speed estimation, speed production, time estimation, time production, distance estimation, monitoring ability, perceptual consistencies and spatial orientation. The measures may consist of absolute thresholds, difference thresholds, as well as other types of psychophysical Indexes.

Figure 3:
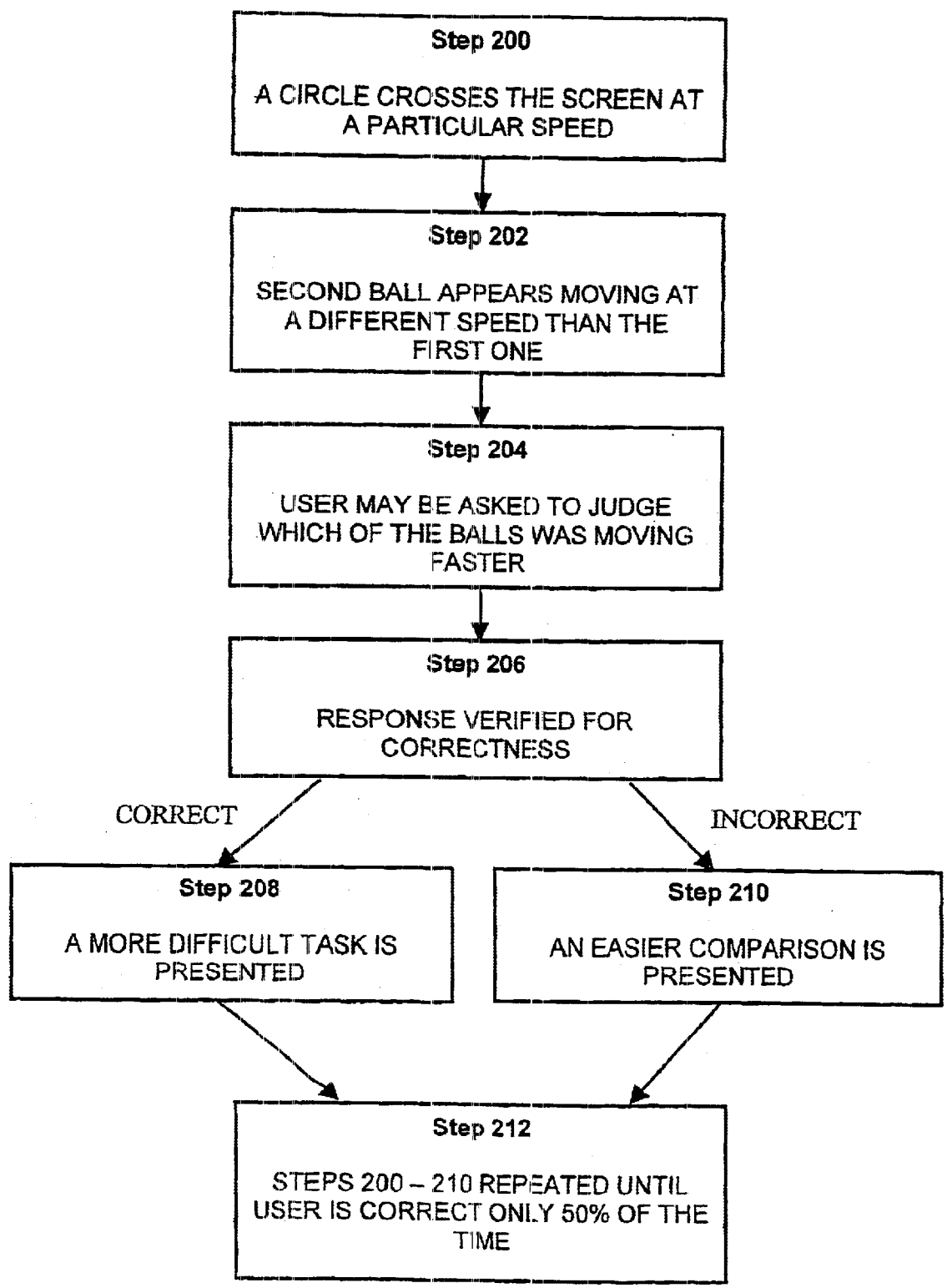

Example of tasks concerned with the above skills are described below:

Difference threshold tasks (for speed)—FIG. 3 as described above, illustrates a system and method that may be used for measuring and training this skill.

Figure 6:
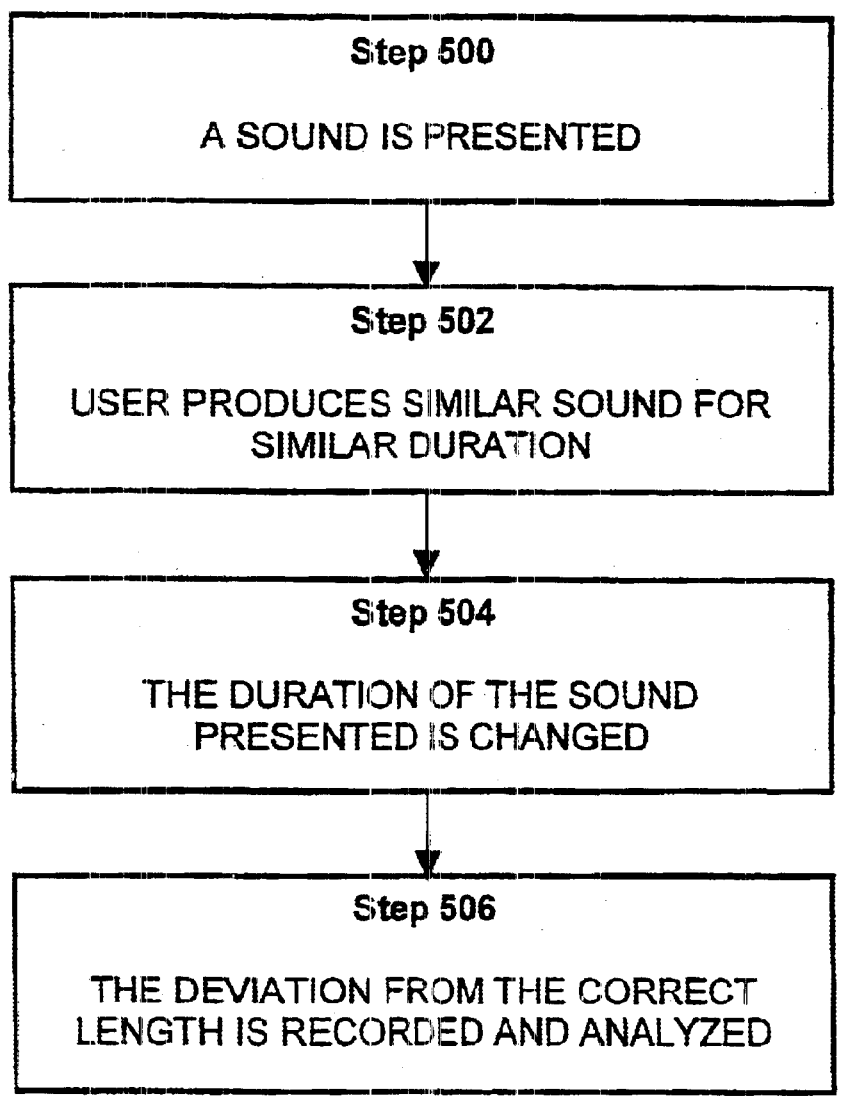

Time production—Referring now to FIG. 6, a sound may be presented for a certain amount of time (step 500). The user may produce a sound that is similar in duration to the presented sound (step 502). The user may produce the sound by pressing the "play" and stop buttons that are displayed on the screen (using a mouse, Joystick, and/or foot pedal or other device). The length of the sound presented by the system may vary between trials (step 504). The deviation of the user's response from the correct duration is recorded and analyzed (step 506).

Speed estimation—An illustration may be shown on a screen of two objects, such as cars, approaching a common point from opposite directions and at different speeds. The user may estimate the speed and distance of the two objects from each other and from the common point, and may indicate (for example by "clicking" Yes or No) whether the first object would have time to arrive at the common point and turn to the left before the second object arrives at the common point. The correctness of the user's choices may be recorded and analyzed.

Time estimation (also a difference threshold task for auditory stimulus)—Two sounds may be presented by the system to the user, who may indicate which one was longer. The difference in the two sound lengths may be varied during the task, and may be changed for every trial. The user's responses may be recorded and analyzed.

Absolute threshold (for symbol identification)—A road sign may be shown moving across the screen for a short time. After it disappears two or more signs, such as four, may be presented and the user may choose which one of the four signs, if any, is the one presented before.

Attention Skills

The present invention may be used for measuring, training and maintaining a wide range of attention skills, including: divided attention (between modalities and within modalities), selective attention, focused attention, sustained attention, peripheral awareness, vigilance.

Examples of tasks concerned with the above skills:

Divided attention (between modalities)—A picture of an object may be presented simultaneously with a sound of a name of the same or of another object. The user indicates whether or not the visual and the auditory stimuli represent the same object. The time taken for a correct answer may be measured and the results analyzed.

Selective attention—A yellow circle may be presented on the screen, which may be in a different place for each trial. The user may move the cursor to the circle and clicks on it. Several visual distractions may appear on the screen during the task. The user has to use selective attention in order to minimize the effect of the distractions. The user's responses may be recorded and analyzed.

Sustained attention—A moving yellow circle may be presented on the screen. The user may track its movement, with, for instance, a mouse cursor or a stylus, for a sustained period of time. The accuracy of this tracking may be recorded and analyzed. The point at which performance decline is detected determines the duration of efficient sustained attention. It is noted that references in these example to color and/or shape are incidental, and any other color, shapes or appropriate stimuli could be interchanged with the mentioned stimuli and still be within the principles of this invention.

Memory Skills

The invention may be used for measuring, training and maintaining a wide range of memory skills, including: explicit and implicit memory, STM, role of clustering in memory, memory mnemonics, recall ability, face recognition, object recognition, pattern recognition, digit span, priming, and location memory.

Examples of tasks that concern with the above skills:

Digit span—On the screen may be presented a line of circles, with a digit on each of them. In each part of the task, a few of the digits briefly light up sequentially. The user may attempt to repeat the same or reverse order using any applicable peripheral device. The number of digits that the user repeats may increase with each trial. The number of digits a user can repeat without errors determines his or her forward or backward digit span.

Location memory—A number of similar circles may be randomly dispersed on the screen. In each part of the task, a few circles may light up in a sequence and the user may repeat, either forward or backward, the location order using the mouse/cursor. The number of circles whose location is to be repeated may increase from trial to trial. The number of circles whose location the user repeats without errors may determine his or her forward or backward short-term location memory.

Object recognition—A picture with many objects may be displayed on the screen for a short time. The user may indicate which of the objects (from a list of objects) appeared. The responses may be coded for correct responses, as well as for false positive and false negative responses, providing a measure of object-recognition ability.

Priming—A group of letters may be presented on the screen. The user may indicate as quickly as possible whether those letters form a meaningful word or have no meaning at all. Some of the meaningful words may follow words from the same class of meanings, for example, the word "chair" might be presented after the word "table". The responses may be recorded and analyzed. Users with good priming abilities are those faster to recognize words that have been so primed.

Semantic and location memory—10 pictures of different objects may be displayed on the screen for a given duration. The user may indicate which of them is not from the same class as the others and where it was located on the screen. The responses may be recorded and analyzed. The number of correct responses and the speed of decision-making are measures of the efficiency of semantic and location memory.

Semantic memory—A group of letters may be presented on the screen. The user may indicate as quickly as possible whether those letters create a meaningful word or have no meaning at all.

Linguistic Skills

The invention may be used for measuring, training and maintaining a wide range of linguistic skills, Including fluency, comprehension, and naming.

Examples of tasks concerned with the above skills:

Comprehension skills—An incomplete sentence may be presented on the screen. The user may indicate which of 4 words presented can be used to complete the sentence. The responses may be analyzed.

Naming—Objects may be presented on the screen one after the other. The user may say the name of each object as quickly as possible. The speed of response and the number of errors may be used to determine naming ability.

Fluency—The user may be asked to list as many objects from the same class as possible, during a particular time interval, for example, all the fruits he can name during one minute.

Decision-making and Problem-solving Skills

The invention may be used for measuring, training and maintaining a wide range of decision-making and problem-solving skills, including: speed of decision, quality of decision, decision style (risk seeking and risk aversion), inhibition skills, switching from automatic to controlled behavior, and planning.

Examples of tasks concerned with the above skills:

Speed of decision—Almost all of the tasks may involve a speed-of-decision measure. For example, two objects may be presented on the screen moving at different speeds and approaching a common point from opposite directions. The screen may then be "frozen", and the user may indicate whether or not the first object, for example, would have had time to reach the common point and turn left before the second object arrived at the common point. The time between the "freezing" of the picture and the beginning of the response determines the decision speed.

Inhibition skills—A circle may be presented on the screen. The user may move the mouse cursor on the circle and click only when, for example, the circle color is yellow. Sometimes the color of the circle may change as the cursor approaches the circle, and the user may attempt to inhibit his or her response.

Route planning—Displayed on the screen may be, for example, a yellow circle, a bell, and various other objects moving across the screen. Using the mouse cursor, the user may bring the yellow circle to the bell (the target) without hitting any of the moving objects. With each task, the bell may move to a new location on the screen. In order to do the task quickly and without errors, the user may dynamically plan the route of movement.

Discrimination efficiency—Two circles of different size may be presented on the screen. The user may choose the smaller one and click on it with the mouse cursor. The time from the introduction of the circle to the beginning of the cursor movement towards the small circle may be used to determine the discrimination time by comparing it to the time taken in a similar task when only one circle is presented.

Psychomotor Skills

The Invention may be used for measuring, training and maintaining a wide range of motor skills, including: simple/discrete motor skills, such as moving objects (changing their location), holding, pushing and pulling; complex/continuous motor skills, such as positioning (operating a control that has discrete states), adjusting; (operating a continuous control), typing (operate a keyboard), and eye-hand coordination, eye-eye coordination, and eye-foot coordination.

Examples of tasks concerned With the above skills:

Discrete motor—Almost all tasks may involve clicking the mouse.

Continuous control—A moving circle may be presented on the screen inside boundaries. The user may track the movement using continuous control. The tracking may be with any of various peripheral devices such as a mouse, a stylus, or a steering wheel.

Complex movement—An object may be displayed on the screen. The user may bring the cursor to the object as quickly as possible. This requires from the user a fast and precise movement and fine correction until the cursor is on the object.

Meta—cognitive Skills

The invention may be used for measuring, training and maintaining meta-cognitive skills, including appropriate confidence level in the correctness of responses.

Example of a task concerned with the above skills:

Confidence level—In the speed-estimation task and the sound-duration estimation task, after making the decision, the user may indicate the level of his or her confidence in the correctness of the response. It may be expected that confidence levels would be higher for correct than for wrong responses. The precise correspondence between confidence levels and correctness may provide a sensitive indication of this skill.

It is noted that for all the embodiments listed herein it may be possible to record and analyze the responses. For some embodiments the responses may be recorded and comparison made either to previous trials of the same user, or to other user's. In such a manner it may be possible to compare the decline in cognitive abilities due to "normal" aging to that due to alcohol and drug related decline, as well as dementia or other diseases. In addition, user's for whom there is historical data about their performance, may receive early warnings about specific decline in their cognitive and psychomotor skills.

Driving Example

One of the embodiments of the present invention focuses on driving-related PCS. Driving is a complex mental activity with exacting demands. In addition to the physical requirements of driving, it may require sufficiently fast reaction time, the ability to judge distance and speed, dual tasking, the ability to pay attention to two or more things at once, and the ability to sort out vital information from distractions—all the while, keeping in mind where one is going and how to get there.

As such, one of the embodiments of the present invention is a computer-based testing and training module focusing on a wide range of cognitive and psychomotor skills necessary for effective driving. In contrast to prior art simulators, the present invention may challenge trainees to develop and maintain the basic psychomotor skills that are at the basis of effective driving. Some of the driving skills that may be trained in the present invention, and which may demonstrate age-related decline are:

Motor skills: Examples thereof include hands and feet dexterity, hand-hand coordination, hand-eye coordination, and smooth movement. As the amount of driving may decrease with age, there may be a corresponding drop in motor performance. Systematic practice of movements related to driving may reduce this loss.

Reaction time: Simple reaction time may be a specific response to the occurrence of a specific stimulus. Complex reaction time may be typically the need to choose the appropriate action from a set of alternatives. In an exemplary embodiment both of these skills may be trained.

Visual attention: Examples of visual attention skills comprise skills such as speed of target detection, divided attention and distractibility, and peripheral awareness.

Route planning: In order to avoid last moment overload on attention and decision making, user's may be coached in route planning, as well as mental rotation, to facilitate return journeys.

Sensory skills: Among these skills may be scene perception, signposts reading, speed estimation, time estimation, and distance estimation. Also included within examples for training of these skills may be the embodiment depicted in Example 3 of Perception skills, The user may also indicate how confident they are that the given response is correct.

The exemplary embodiment may control the difficulty of each segment by varying one or more of the following parameters:

(1) Duration of exposure to the scene
(2) Absolute speeds of the two cars
(3) Difference between their respective speeds
(4) Distance from the intersection prior to stopping the movement
(5) The obviousness of the correct answer. As such, if the correct answer is that it is safe to make the turn, what would be the minimal distance between the two cars? If the correct answer is that it is unsafe to make the turn, how much will the other car have to reduce its speed in order to avoid collision?

On-line diagnostics may distinguish between two kinds of errors: false positive (i.e. deciding to make the turn when it wasn't safe) and false negative (i.e. deciding to stop when it wasn't necessary).

The present invention may also be implemented to check other types of information about a particular user, such as to ascertain whether tendencies towards "risk taking" or "conservatism" are task specific or more general traits.

On the basis of these on-line diagnostics the present invention may be used to explain to the user his/her particular biases and problems, and may proceed to present tasks aimed at dealing with these problems, as well as provide the option of giving specific information about research on risk taking. Subsequent training may focus on the particular type of error of the user in order to reduce it.

At some point, issues of distractibility may be introduced into the training. This may be accomplished via presentation of additional information that, although irrelevant to the task, may distract the user's attention. Visual and/or auditory stimuli of varying degrees of distractiveness may be presented at critical moments, making the task progressively more demanding.

The Apparatus and System

It is apparent to those skilled in the art that the function of the mouse may be interchanged with that of other peripheral devices, such as a keyboard, joystick, foot pedal, stylus, etc. These peripheral devices may create extensive possibilities for testing and training of motor skills, and may facilitate monitoring and controlling of cognitive skills in a manner that was impossible on prior art keyboard-based systems.

For example, the present invention may use the various devices to test a wide range of motor skills such as moving objects (changing location), and/or complex/continuous motor skills such as positioning (operating a control which has discrete states) or adjusting (operating with a continuous control). The present invention may also measure moving time, movement smoothness, complex eye hand coordination, hand-hand coordination, eye foot coordination and more.

The system may comprise software, as well as a combination of software and hardware, e.g.: specially adapted joysticks, pedals, microphones, etc. It additionally may be set up to function as a stand-alone module located at a user's home, a medical facility, a therapeutic center, or any other appropriate location. It additionally may comprise an Interconnected system of one or more workstations. The system may comprise adaptable computer programs accessible to the computers/work stations via either CDs, internet, intranet, or any other method for transporting information.

The present invention may also be provided as customized individual packages, as well as multiple workstations connected to a network in retirement homes and communities, or health clubs. An Internet address specifically dedicated to training may be yet another venue.

The present invention may also comprise a database that may store the responses and possibly historical performance of each user. The database may be local or may be remote, and may be accessible via the Internet or may be fully or partially available at a user's facilities. In one embodiment the database may be run by a large organization and may accumulate the histories and response of many individuals, thereby providing for the possible creation of a database of across-the-board norms. The database may be used to compare the stored responses with the current user's responses so as to facilitate cross-validation of the user's test results against currently acceptable diagnostic criteria.

In such a manner it may be possible to diagnose the current user's deviation from the normal, and possibly be used as a tool for diagnosing posttraumatic deficit (following stroke or head injury) dementia, Alzheimer's disease, Parkinson disease (particularly, but not exclusively, with high resolution testing of smooth movement), behavioral disorders such as Hyperactivity and Attention Deficit Disorder (particularly, but not exclusively, with the cluster of tests dealing with attentional skills), or learning disabilities such as dyslexia, dysgraphia or dyscalculia (primarily, but not exclusively, with tests measuring fluency, and naming). The uses of the data base are not limited to these applications, and enclosed within the principle of the present invention are other applications thereof.

It is noted that the present invention may be operable from a mobile storage device, such as a CD or floppy, or may be accessible from a mainframe or via public communication networks, such as the Internet. Additionally, the present invention may be practiced by a single person, or an organization, and the database may be centralized, localized, and/or held by either an internal or external organization.

It will be appreciated by persons skilled in the art that the present invention is not limited to what has been particularly shown and described hereinabove. Rather, the scope of the present invention is defined only by the claims which follow:

What is claimed is:

1. A method for diagnosing and training cognitive ability of a user, the method comprising:
    presenting a stimulus;
    receiving a motion input generally in response to said stimulus;
    analyzing cognitive skills of said motion input for a diagnosis
    to selecting one or more tasks to train said cognitive skills.

2. A method according to claim 1, wherein the step of presenting is selected from a group consisting of: presenting a moving stimulus, presenting a stimulus which changes color, presenting a stimulus which changes shape, presenting one or more stimuli and presenting stimuli targeting different senses.

3. A method according to claim 1, wherein said motion input is selected from a group consisting of: moving said stimulus, positioning said stimulus, moving a peripheral device to intercept said stimulus, operating a control with discrete states, and adjusting said stimulus.

4. A method according to claim 1 wherein said stimulus is selected from a group consisting of: one or more abstract stimuli, one or more meaningful stimuli and a combination of said one or more abstract stimuli with said one or more meaningful stimuli.

5. A method according to claim 1, wherein said cognitive skills are selected from a group consisting of: motor skills, complex/continuous motor skills, time required to move said stimulus, movement smoothness, complex eye hand coordination, hand-hand coordination, eye-foot coordination, psychomotor skills perceptual skills, attention skills, memory skills, linguistic skills, decision making/problem solving skills, psychomotor skills, and meta-cognitive skills.

6. A method according to claim 1, further comprising the step of:
    determining from said cognitive skills a cognitive level of said user.

7. A method according to claim 1, wherein said step of analyzing comprises the steps of:
    testing a preliminary cognitive level of said user and receiving results representative therefrom;
    breaking up said results to separate discrete cognitive skills;
    and wherein said step of selecting comprises the steps of:
        according to said results, creating one or more tasks related to each of said separate discrete cognitive skills;
        presenting one or more tasks to said user; and
        re-testing a current cognitive level of said user and receiving results representative therefrom.

8. A method according to claim 7, wherein the step of creating comprises the steps of:
    creating a first task which trains a first cognitive skill and
    using results of said first task as parameters for one or more other tasks.

9. A method according to claim 7, further comprising the steps of:
    updating said step of presenting in accordance with results from said step of analyzing; and
    repeating said steps of presenting, receiving, analyzing, determining and updating one or more times.

10. A method according to claim 7, further comprising the step of:
    customizing the step of presenting for each said user in accordance with results to said step of analyzing.

11. A method according to claim 9, further comprising the step of:
    customizing said step of presenting to generally optimally challenge said cognitive level of said user.

12. A method according to claim 9, wherein said step of updating comprises controlling selection of said stimulus in order to attempt to avoid frustration or boredom of said users.

13. A method according to claim 1, wherein said step of analyzing comprises differentiating between a false positive error and a false negative error.

14. A method according to claim 1, wherein said method is used to diagnose dementia, Alzheimer's disease, Parkinson disease, Hyperactivity, Attention Deficit Disorder, and learning disabilities.

15. A computer software storage device comprising a program, said program being configured to present stimulus to a user, to receive a motion input generally in response to said stimulus and to analyze cognitive aspects of said motion input.

16. A method of diagnosing and training cognitive levels of a user, the method comprising:
presenting a stimulus;
receiving a motion input generally in response to said stimulus;
analyzing cognitive skills of said motion input for a diagnosis; said analyzing comprising:
testing a preliminary cognitive level of said user and receiving results representative therefrom;
breaking up said results to separate discrete cognitive skills;
according to said results, creating one or more tasks intended to train one or more of said separate discrete cognitive skills;
presenting one or more tasks to said user; and
updating said step of presenting in accordance with results from said step of analyzing; and
repeating said steps of processing, receiving, analyzing and updating so that selected discrete cognitive skills are re-presented for improving the user's cognitive level.

17. A method for diagnosing and training cognitive ability, the method comprising:
testing a preliminary cognitive level of a user and receiving results for a diagnosis;
breaking up said results to separate discrete cognitive skills;
according to said results, creating one or more tasks intended to train one or more of said separate discrete cognitive skills;
presenting one or more tasks to said user;
re-testing a current cognitive level of said user and receiving results representative therefrom.

18. A method according, to claim 17 and further comprising the step of repeating said steps of breaking up, creating, presenting and retesting at least one time.

19. A method according to claim 17, wherein said separate discrete cognitive skills comprise perceptual skills, attention skills, memory skills, linguistic skills, decision making/problem solving skills, psychomotor skills, and meta-cognitive skills.

20. A method according to claim 17, wherein the step of creating comprises the steps of:
creating a first task which trains a first cognitive skill and using results of said first task to control one or more other tasks.

21. A method according to claim 17, further comprising determining an optimal challenge level based on results from the step of re-testing.

22. A method according to claim 17, wherein said method is performed one or more times a week.

23. A method according to claim 17, wherein said method is used in treating dementia, Alzheimer's disease, Parkinson disease, Hyperactivity, Attention Deficit Disorder, and learning disabilities.

24. A method according to claim 17, wherein said method is used in cognitive rehabilitation following stroke, head injury, and alcohol and drug abuse.

25. A method according to claim 17, wherein said method is used to enhance or postpone decline of short term memory, perceptual abilities, and other cognitive and psychomotor abilities in people of all ages.

26. A system for training and diagnosing cognitive ability, the system comprises:
a motion input device;
an output device which provides a stimulus, said stimulus is affected by a user manipulating said input device;
an analyzer which analyzes data from said input device and diagnoses therefrom cognitive levels; and
a computing unit which assigns tasks to be executed by said user, wherein said tasks are intended to train said cognitive levels of said user.

27. A system according to claim 26, further comprising a voice recording device.

28. A system according to claim 26, further comprising a processor which determines from said analyzed data said stimulus appropriate for said cognitive level.

29. A system according to claim 26, wherein said motion input device is selected from a group consisting of: a mouse, a joystick, a foot pedal, a digital pen, a stylus, a motion pad and a steering wheel.

30. A system according to claim 26, wherein said analyzed data comprises data regarding motor skills, complex/continuous motor skills, time required to move said stimulus, movement smoothness, complex eye hand coordination, hand-hand coordination, and eye-foot coordination.

31. A system according to claim 26, further comprising a database for storing said analyzed data.

32. A system according to claim 31, wherein said stored analyzed data comprises data related to cognitive norms.

33. A method for diagnosing and training cognitive ability of a user, said method comprising:
testing a cognitive level of a user;
comparing said cognitive level to analyzed data stored in a database for a diagnosis, and
creating one or more tasks in accordance with said cognitive level, said tasks for training said cognitive level of said user.

34. A method according to claim 33, wherein said method is used to diagnose dementia, Alzheimer's disease, Parkinson disease and learning disabilities.

35. A method for diagnosing cognitive skills and training driving skills of a user, the method comprising the steps of:
presenting stimuli relevant to driving situations;
receiving motion input from said user in response to said stimulus;
analyzing cognitive aspects of said input for diagnosis;
interpolating said analyzed aspects into cognitive skills applicable for, driving skills;
adjusting said stimulus according to said analyzed aspects;
selecting one or more tasks to train said cognitive skills applicable for driving skills;
executing said one or more tasks; and
repeating said presenting, receiving, analyzing, interpolating, adjusting, selecting and executing one or more times.

36. A method according to claim 35, further method comprising the steps of:
recording the number and type of mistaken responses and recording the speed of reaction; and
distinguishing between false positive errors and false negative errors.

* * * * *